US012367597B2

(12) United States Patent
Yan

(10) Patent No.: US 12,367,597 B2
(45) Date of Patent: Jul. 22, 2025

(54) TRACKERLESS 2D ULTRASOUND FRAME TO 3D IMAGE VOLUME REGISTRATION

(71) Applicant: Rensselaer Polytechnic Institute, Troy, NY (US)

(72) Inventor: Pingkun Yan, Clifton Park, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 368 days.

(21) Appl. No.: 17/793,215

(22) PCT Filed: Jan. 15, 2021

(86) PCT No.: PCT/US2021/013541
§ 371 (c)(1),
(2) Date: Jul. 15, 2022

(87) PCT Pub. No.: WO2021/146497
PCT Pub. Date: Jul. 22, 2021

(65) Prior Publication Data
US 2023/0081648 A1    Mar. 16, 2023

Related U.S. Application Data

(60) Provisional application No. 63/137,403, filed on Jan. 14, 2021, provisional application No. 62/961,382, filed on Jan. 15, 2020.

(51) Int. Cl.
*G06T 7/30* (2017.01)
*G06T 7/70* (2017.01)

(52) U.S. Cl.
CPC .................. *G06T 7/30* (2017.01); *G06T 7/70* (2017.01); *G06T 2200/04* (2013.01);
(Continued)

(58) Field of Classification Search
None
See application file for complete search history.

(56) References Cited

U.S. PATENT DOCUMENTS 7,480,398 B2    1/2009   Kleen et al.
8,050,483 B2    11/2011  Boese et al.
(Continued)

FOREIGN PATENT DOCUMENTS

WO    2019101836 A1    5/2019
WO    2019219387 A1    11/2019

OTHER PUBLICATIONS

International Search Report and The Written Opinion of the International Searching Authority, International Application No. PCT/US2021/013541, mailed Apr. 5, 2021.
(Continued)

*Primary Examiner* — Lennin R Rodriguezgonzalez
(74) *Attorney, Agent, or Firm* — Barclay Damon LLP; Anthony P. Gangemi

(57) ABSTRACT

One embodiment provides an apparatus for registering a two dimensional (2D) ultrasound (US) frame and a three dimensional (3D) magnetic resonance (MR) volume. The apparatus includes a first deep neural network (DNN) and an image fusion management circuitry. The first DNN is configured to determine a 2D US pose vector based, at least in part, on 2D US frame data. The image fusion management circuitry is configured to register the 2D US frame data and a 3D MR volume data. The registering is based, at least in part, on the 2D US pose vector.

20 Claims, 6 Drawing Sheets

(52) U.S. Cl.
CPC ............ *G06T 2207/10088* (2013.01); *G06T 2207/10132* (2013.01); *G06T 2207/20016* (2013.01); *G06T 2207/20081* (2013.01); *G06T 2207/20084* (2013.01); *G06T 2207/20221* (2013.01); *G06T 2207/30081* (2013.01)

(56) References Cited

U.S. PATENT DOCUMENTS

| | | |
|---|---|---|
| 8,184,886 B2 | 5/2012 | Khamene et al. |
| 8,620,055 B2 | 12/2013 | Barratt et al. |
| 8,666,128 B2 | 3/2014 | Chaney et al. |
| 8,731,264 B2 | 5/2014 | Kruecker et al. |
| 8,818,105 B2 | 8/2014 | Myronenko et al. |
| 8,948,471 B2 | 2/2015 | Fichtinger et al. |
| 9,135,706 B2 | 9/2015 | Zagorchev et al. |
| 9,240,046 B2 | 1/2016 | Carrell et al. |
| 9,271,686 B2 | 3/2016 | Majewski et al. |
| 9,282,944 B2 | 3/2016 | Fallavollita et al. |
| 9,418,468 B2 | 8/2016 | Paragios et al. |
| 9,572,548 B2 | 2/2017 | Moctezuma de la Barrera |
| 9,681,919 B2 | 6/2017 | Glossop |
| 10,151,580 B2 | 12/2018 | Wong et al. |
| 2013/0211230 A1 | 8/2013 | Sperling |
| 2013/0310679 A1 | 11/2013 | Natarajan et al. |
| 2016/0143576 A1 | 5/2016 | Symon et al. |
| 2016/0260014 A1 | 9/2016 | Hagawa et al. |
| 2019/0159752 A1 | 5/2019 | Bharat et al. |
| 2019/0295702 A1 | 9/2019 | Das et al. |
| 2020/0146635 A1 | 5/2020 | Wang et al. |

OTHER PUBLICATIONS

Xue, E.Y., "Sensorless Ultrasound Probe 6DoF Pose Estimation Through the Use of CNNs on Image Data," Massachusetts Institute of Technology, Jun. 2018.

TRACKERLESS 2D ULTRASOUND FRAME TO 3D IMAGE VOLUME REGISTRATION

CROSS REFERENCE TO RELATED APPLICATION(S)

This application claims the benefit of U.S. Provisional Application No. 62/961,382, filed Jan. 15, 2020, and U.S. Provisional Application No. 63/137,403, filed Jan. 14, 2021, which are incorporated by reference as if disclosed herein in their entireties.

GOVERNMENT LICENSE RIGHTS

This invention was made with government support under award number EB028001 and award number EB027898, both awarded by the National Institute of Biomedical Imaging and Bioengineering (NIBIB) of the National Institutes of Health, and through an NIH Bench-to-Bedside award made possible by the National Cancer Institute. The government has certain rights in the invention.

FIELD

The present disclosure relates to image registration, in particular to, trackerless two-dimensional (2D) ultrasound frame to three dimensional (3D) image volume registration.

BACKGROUND

About 3 million American men suffer from prostate cancer, the second leading cause of cancer death for men in the United States. If prostate cancer is detected at an early stage, before it spreads to other parts of the body, there is a considerable chance of survival. However, an estimated 22% to 47% of the patients with negative biopsies but elevated prostate-specific antigen levels may still harbor malignant tumors, which is life-threatening. Commonly used ultrasound-guided random biopsy has the potential to miss the detection of such malignant tumors. By contrast, the fusion of magnetic resonance imaging (MRI) and ultrasound (US) for guiding targeted biopsies has shown to significantly improve the cancer detection rate. The application of MRI-TRUS fusion itself, however, is very challenging, which results from the difficulties in directly registering images of these two very different modalities in different dimensions.

SUMMARY

In some embodiments, there is provided an apparatus for registering a two dimensional (2D) ultrasound (US) frame and a three dimensional (3D) magnetic resonance (MR) volume. The apparatus includes a first deep neural network (DNN) and an image fusion management circuitry. The first DNN is configured to determine a 2D US pose vector based, at least in part, on 2D US frame data. The image fusion management circuitry is configured to register the 2D US frame data and a 3D MR volume data. The registering is based, at least in part, on the 2D US pose vector.

In some embodiments, the apparatus further includes a second DNN, a 3D US volume reconstruction circuitry and a third DNN. The second DNN is configured to determine a 3D US pose vector based, at least in part, on the 2D US frame data. The 3D US volume reconstruction circuitry is configured to reconstruct a 3D US volume based, at least in part, on the 3D US pose vector. The third DNN is configured to determine a transformation relating the 3D MR volume and the 3D US volume. The registering is based, at least in part, on the transformation.

In some embodiments of the apparatus, the first DNN and the second and third DNNs are trained alternatingly.

In some embodiments of the apparatus, the third DNN includes a plurality of DNN stages configured for coarse-to-fine multi-stage registration.

In some embodiments of the apparatus, the third DNN is configured as a generative adversarial network (GAN).

In some embodiments of the apparatus, the first DNN is initially trained using population data and is subsequently trained using patient data.

In some embodiments, there is provided a method for registering a two dimensional (2D) ultrasound (US) frame and a three dimensional (3D) magnetic resonance (MR) volume. The method includes determining, by a first deep neural network (DNN), a 2D US pose vector based, at least in part, on 2D US frame data. The method further includes registering, by an image fusion management circuitry, the 2D US frame data and a 3D MR volume data. The registering is based, at least in part, on the 2D US pose vector.

In some embodiments, the method further includes determining, by a second DNN, a 3D US pose vector based, at least in part, on the 2D US frame data; reconstructing, by a 3D US volume reconstruction circuitry, a 3D US volume based, at least in part, on the 3D US pose vector; and determining, by a third DNN, a transformation relating the 3D MR volume and the 3D US volume. The registering is based, at least in part on the transformation.

In some embodiments of the method, the first DNN and the second and third DNNs are trained alternatingly.

In some embodiments of the method, the third DNN comprises a plurality of DNN stages configured for coarse-to-fine multi-stage registration.

In some embodiments of the method, the third DNN is configured as a generative adversarial network (GAN).

In some embodiments of the method, the first DNN is initially trained using population data.

In some embodiments of the method, the first DNN is trained using patient data.

In some embodiments, there is provided a system for registering a two dimensional (2D) ultrasound (US) frame and a three dimensional (3D) magnetic resonance (MR) volume. The system includes a processor; a memory; input/output circuitry; a first deep neural network (DNN) and an image fusion management circuitry. The first DNN is configured to determine a 2D US pose vector based, at least in part, on 2D US frame data. The image fusion management circuitry is configured to register the 2D US frame data and a 3D MR volume data. The registering is based, at least in part, on the 2D US pose vector.

In some embodiments, the system further includes a second DNN, a 3D US volume reconstruction circuitry and a third DNN. The second DNN is configured to determine a 3D US pose vector based, at least in part, on the 2D US frame data. The 3D US volume reconstruction circuitry is configured to reconstruct a 3D US volume based, at least in part, on the 3D US pose vector. The third DNN is configured to determine a transformation relating the 3D MR volume and the 3D US volume. The registering is based, at least in part on the transformation.

In some embodiments of the system, the first DNN and the second and third DNNs are trained alternatingly.

In some embodiments of the system, the third DNN comprises a plurality of DNN stages configured for coarse-to-fine multi-stage registration.

In some embodiments of the system, the third DNN is configured as a generative adversarial network (GAN).

In some embodiments of the system, the first DNN is initially trained using population data and is subsequently trained using patient data.

In some embodiments, there is provided a computer readable storage device. The device has stored thereon instructions that when executed by one or more processors result in the following operations including: any embodiment of the method.

BRIEF DESCRIPTION OF DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

Although the following Detailed Description will proceed with reference being made to illustrative embodiments, many alternatives, modifications, and variations thereof will be apparent to those skilled in the art.

DETAILED DESCRIPTION

As is known, different imaging modalities, e.g., 2D US frames and/or 3D MR images, can have very different characteristics not only because of the different imaging technologies but also the different dimensionality (i.e., 2D versus 3D). In prostate biopsies for example, registering a 2D US frame with a corresponding 3D MR volume can facilitate making an accurate diagnosis. During a prostate biopsy, as the target prostate is being scanned, a position and an orientation of an ultrasound probe vary (i.e., are not fixed). In contrast, the corresponding 3D MR volume (captured prior to the ultrasound guided biopsy) may be considered fixed during the prostate biopsy. Thus, registration of a 2D US frame with a corresponding 3D MRI volume may present challenges related to the different imaging technologies and different dimensionality as well as relative movement.

Generally, this disclosure relates to image fusion and, in particular, to trackerless two-dimensional (2D) ultrasound frame to three dimensional (3D) image volume registration. A method, apparatus, and/or system may be configured to implement both population-based learning and patient specific registration to provide relatively accurate alignment of 2D US frame data and 3D MR volume data. The 2D US frames may include, but are not limited to, transrectal (TR) US frames, transabdominal (TA) US frames, transperineal (TP) US frames, etc.

In one embodiment, the image fusion may be performed directly and, in another embodiment, the image fusion may be performed indirectly. As used herein, "direct image fusion" corresponds to registering a 2D US frame with a corresponding 3D MR volume. As used herein, "indirect image fusion" corresponds to reconstructing a 3D US volume based, at least in part, on a plurality of 2D US frames and utilizing the reconstructed 3D US volume for registration with the 3D MR volume. It may be appreciated that direct image fusion and indirect image fusion may be complementarity so that using both may provide a relatively better output.

In an embodiment, there is provided an apparatus for registering a two dimensional (2D) ultrasound (US) frame and a three dimensional (3D) magnetic resonance (MR) volume. The apparatus includes a first deep neural network (DNN) and an image fusion management circuitry. The first DNN is configured to determine a 2D US pose vector based, at least in part, on 2D US frame data. The image fusion management circuitry is configured to register the 2D US frame data and a 3D MR volume data. The registering is based, at least in part, on the 2D US pose vector.

Figure 1A:
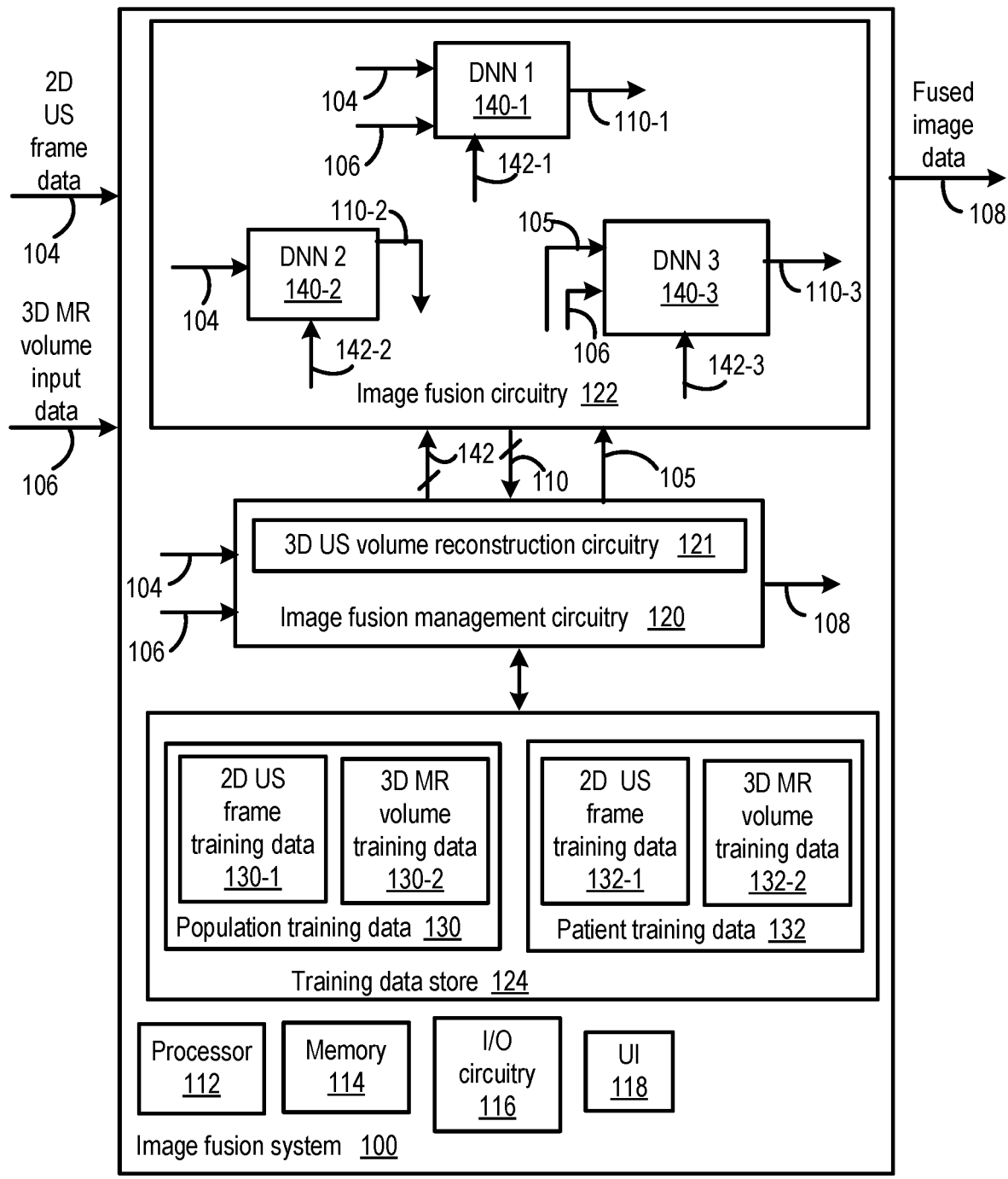
FIG. 1A illustrates a functional block diagram of an image fusion system consistent with several embodiments of the present disclosure.

FIG. 1A illustrates a functional block diagram of an image fusion system 100 consistent with several embodiments of the present disclosure. In an embodiment, image fusion system 100 is configured to receive two dimensional (2D) ultrasound (US) frame data 104 and three dimensional (3D) magnetic resonance (MR) image volume data 106 and to provide as output fused image data 108 corresponding to the 2D ultrasound US frame data fused (i.e., registered) with the 3D MR image volume data.

Image fusion system 100 includes a processor 112, a memory 114, input/output (I/O) circuitry 116, and a user interface (UI) 118. Image fusion system 100 includes image fusion management circuitry 120, and image fusion circuitry 122. In some embodiments, image fusion management circuitry 120 may include 3D US volume reconstruction circuitry 121. Image fusion circuitry 122 includes a plurality of deep neural networks (DNNs), e.g., DNN1 140-1, DNN2 140-2, and DNN3 140-3. In some embodiments, one or more of DNNs 140-1, 140-2, 140-3 may correspond to a convolutional neural network (CNN).

Image fusion system 100 may further include a training data store 124. For example, the training data store 124 may be included during training DNNs 140-1, 140-2, 140-3. Training data store 124 may be configured to store population training data 130 and patient training data 132. Population training data 130 may include 2D US frame training data 130-1, and 3D MR volume training data 130-2 corresponding to a group of patients, i.e., population. Patient training data 132 may include 2D US frame training data 130-1, and 3D MR volume training data 130-2 for a selected patient. Each 2D US frame training data set may include 2D US frame data and corresponding registration data associated with each frame. Each 3D MR volume training data set may include 3D MR image volume data. For example, training data may include 3D location data associated with each training 2D US frame captured using an electromechanical system. In another example, training data may include expert registration corresponding to registered training 2D US frame and training 3D MR image pairs. It may be appreciated that such training location and registration data may correspond to "ground truth" data used for training one or more DNNs, as described herein.

Processor 112 may include, but is not limited to, a single core processing unit, a multicore processor, a graphics processing unit, etc. Memory 114 may be configured to store one or more of image fusion management circuitry 120, 3D US volume reconstruction circuitry 121, image fusion circuitry 122 (e.g., DNNs 140-1, 140-2, 140-3), and training data store 124. I/O circuitry 116 may be configured to receive input data 2D US frame data 104, 3D MR volume data 106, and/or to provide estimated output data, i.e., fused image data 108. UI 118 may include a user input device and/or a user output device. A user input device may include, but is not limited to, a mouse, a keyboard, a touchpad, a touch sensitive display, a microphone, a camera, etc. A user output device may include, but is not limited to, a display, a visual indicator (e.g., a light), a loudspeaker, etc.

Each DNN is configured to receive input image data and to provide corresponding output image data. Thus, DNN1 140-1 is configured to receive 2D US frame data 104 and 3D MR volume input data 106 and to provide as output DNN1 output data 110-1. DNN2 140-2 is configured to receive 2D US frame data 104 and to provide as output DNN2 output data 110-2. DNN3 140-3 is configured to receive 3D US volume data 105 and 3D MR volume input data 106 and to provide as output DNN3 output data 110-3. In some embodiments, DNN2 output data 110-2 may correspond to a pose vector related to reconstructed 3D US volume data.

Image fusion management circuitry 120 is configured to manage training and operation of image fusion circuitry 122. Image fusion management circuitry 120 may be configured to provide DNN parameters 142 to image fusion circuitry 122 and to receive DNN output data 110 from image fusion circuitry 122. DNN parameters 142 may include one or more of DNN1 parameters 142-1, DNN2 parameters 142-2, and/or DNN3 parameters 142-3. As used herein, DNN parameters 142 may include hyper parameters. Image fusion management circuitry 120 may be further configured to provide intermediate 3D MR volume data and/or intermediate 3D US volume data to image fusion circuitry 122, and/or to receive one or more pose and/or transformation vectors 110-1, 110-2, 110-3 from image fusion circuitry 122, as will be described in more detail below.

In some embodiments, image fusion management circuitry 120 may include 3D US volume reconstruction circuitry 121. In these embodiments, 3D US volume reconstruction circuitry 121 may be configured to reconstruct a 3D US volume 105 based, at least in part, on 2D US frame data 104. The 2D US frame data 104 may include a plurality of 2D US frames that may be related in time. In some embodiments, each frame may have an associated location and orientation that may be represented by pose vector 110-2. Image fusion management circuitry 120 may be configured to provide the 3D US volume data 105 to image fusion circuitry 122 and to, for example, DNN3 140-3.

During training, image fusion management circuitry 120 may be configured to provide training input data to image fusion circuitry 122 and to receive neural network output data, e.g., one or more of neural network output data 110-1, 110-2, 110-3, from image fusion circuitry 122. Image fusion management circuitry 120 may be further configured to adjust neural network parameters and/or hyper parameters 142-1, 142-2, 142-3, during training based on neural network output data and corresponding training data. Thus, training data 130, 132 may include input data and corresponding ground truth output data.

In some embodiments, DNN1 140-1 may be configured to directly estimate an ultrasound transducer pose. DNN1 140-1 may be configured to determine a pose vector p that includes a 3D position x and an orientation represented by q (quaternion), i.e., p=[x, q]. It may be appreciated that quaternions may be used for orientation representation due to their relative superiority in computing arbitrary rotation. A loss function associated with DNN1 140-1 may then be defined as:

$$L(I_{US-2D}, I_{MR-3D}) = \|\hat{x} - x\|_2 + \alpha \|\hat{q}/\|\hat{q}\| - q/\|q\|\|_2 \qquad (1)$$

where α is a positive weighting parameter and $\hat{x}$ and $\hat{q}$ correspond to ground truth position data and orientation data, respectively. Thus, DNN1 140-1 may be configured to directly estimate pose vector p using 2D US frame data and 3D MR volume data. In other words, the pose vector may be configured to provide relative position and orientation of the 2D US frame with respect to the corresponding 3D MR volume. Image fusion management circuitry 120 may then be configured to fuse the 2D US frame data 104 and the 3D MR volume data 106 to generate the corresponding fused image data output 108 based, at least in part, on the pose vector. The pose vector, p, may thus correspond to DNN1 output 110-1. Thus, DNN1 140-1 may be configured for direct image fusion.

In some embodiments, DNN2 140-2 and DNN3 140-3 may be configured to implement indirect image fusion. DNN2 140-2 may be configured to receive 2D US frame data 104 and to determine a pose vector 110-2 based, at least in part, on the 2D US frame data 104. The pose vector 110-2 may then be provided to the image fusion management circuitry 120. Image fusion management circuitry 120 and, for example, 3D US volume reconstruction circuitry 121, may be configured to generate reconstructed 3D US volume data 105 based, at least in part on the 2D US frame data 104. The reconstructed 3D US volume data 105 may then be provided to DNN3 140-3. The reconstructed 3D US volume data 105 may be positioned and/or oriented based, at least in part, on the pose vector 110-2. DNN3 140-3 may be configured to receive the reconstructed 3D US volume data 105 and the 3D MR volume input data 106 and to determine transformation data relating the reconstructed 3D US volume 105 to the 3D MR volume 106. The transformation data may then correspond to DNN3 output 110-3. Image fusion management circuitry 120 may then be configured to fuse the 2D US frame data 104 and the 3D MR volume input data 106 based, at least in part, on the transformation data 110-3.

In one nonlimiting example, fusing the 2D US frame data and the 3D MR volume data is configured to facilitate directed biopsy of a prostate based, at least in part, on the imaging data.

Figure 1B:
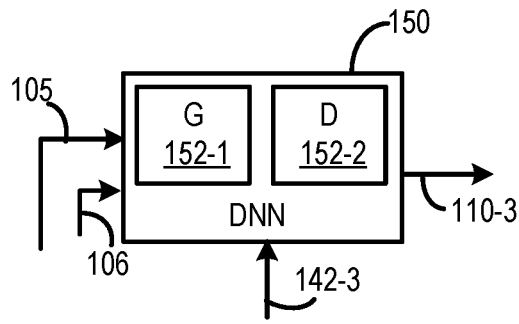
FIGS. 1B and 1C illustrate functional block diagrams of two example deep neural networks consistent with several embodiments of the present disclosure.

The following description may be best understood when considering FIG. 1A and FIG. 1B together. FIG. 1B is a functional block diagram for one example DNN 150 corresponding to DNN3 140-3 of FIG. 1A. In this example, DNN 150 (and thus DNN3 140-3) may correspond to a generative adversarial network (GAN) and may include a generator G 152-1 and a discriminator D 152-2. The discriminator D 152-2 may be understood as an evaluator in this example. DNN 150 may be configured to obtain image registration and quality evaluation simultaneously. In some embodiments, an image registration technique based on the GAN framework may be configured to simultaneously train DNN 150 for transformation parameter estimation and evaluating registration quality. Thus, generator G 152-1 and discriminator D 152-2 may be trained in the adversarial fashion. G 152-1 is configured to directly estimate transformation parameters, $T_{est}$, between an input image pair, i.e., between reconstructed 3D US volume data 105 and 3D MR volume input data 106.

Image fusion management circuitry 120 may then be configured to implement an image resampler. The image resampler is configured to utilize the estimated transform information $T_{est}$ to interpolate a current input moving image, e.g., reconstructed 3D US volume data 105, to generate a new resampled moving image. The discriminator D 152-2 (i.e., evaluator) is configured to assess an alignment of its input image pair given $T_{est}$ and based on a ground truth transformation, $T_{gt}$. The ground truth transformation may be determined based, at least in part, on actual position data (training data) captured from, for example, electromagnetic tracking. As the training progresses, both G 152-1 and E 152-2 are updated iteratively, i.e., image fusion management circuitry 120 is configured to adjust parameters 142-3. Thus, image fusion management circuitry 120 may be configured to determine and utilize a direct supervised loss based, at least in part, on $T_{gt}$. Image fusion management circuitry 120 may be further configured, corresponding to a GAN framework, to adjust the parameters of G 152-1 based, at least in part, on feedback from D 152-2. Eventually G 152-1 may become relatively well trained, configured to generate transformations relatively close to $T_{gt}$ to pass the evaluation of D 152-2.

Advantageously, the GAN architecture of DNN 150 and training technique of this embodiment are configured to estimate transformation parameters with a relatively efficient forward pass of network G 152-1. DNN 150 is further configured to evaluate the quality of the estimated registration with D 152-2. DNN 150, and thus DNN3 140-3 in this example, may be trained in an end-to-end fashion, where both G 152-1 and D 152-2 become available once the training is completed. In other words, both G 152-1 and D 152-2 may correspond to trained DNNS at the completion of the training. The estimated transformation $T_{est}$ may be used as the input for training D 152-2 along with perturbated transformations around the $T_{gt}$, through which D 152-2 (i.e., the evaluator) may learn a distribution of the generated transformations.

It may be appreciated that, with a relatively well-designed cost function and a suitable initialization, classical iterative registration approaches may have a higher likelihood of finding an optimal pose. In some embodiments, classical iterative registration may be combined with the GAN approach. For example, registration estimations may be generated by using the generator G 152-1 and then D 152-2 may be used as a registration metric for classical iterative framework to complete the registration process.

In some embodiments, rigid transformations may be used in some registration techniques. While the prostate deforms differently under MRI and the US imaging, it may cause difficulties for rigid registration, which can be addressed. Rigid registration is commonly used in clinical procedures, and has been shown to be sufficient to obtain clinically significant results. If the deformation presents a severe problem for deep learning-based methods, it is contemplated that prostate segmentation may be introduced to add a label constraint to help improve the registration performance. Deformable registration based on the methodology described herein may be implemented and evaluated.

It may be appreciated that, to begin fusion guided biopsy procedures, physicians generally first sweep through the prostate several times to collect patient specific information open (e.g., locations of cyst, calcification, hyper-/hypo-echoic areas, or any structure with salient shape or texture). Using those anatomical image features for a particular patient allows a better correlation of images from different modalities. Such information has not historically been used in image registration. One reason may be the difficulty in giving supervised intra-procedural feedback on image registration. Some embodiments of the present disclosure are directed to training the registration networks for each particular subject in a self-correcting manner to efficiently learn patient-specific image alignment.

Turning again to FIG. 1A, in some embodiments, image fusion management circuitry 120 may be configured to train image fusion circuitry 122 in two training stages: population-based learning and patient-specific learning. In other words, training image fusion circuitry 122 to fuse intra-procedural 2D US frames with preoperative 3D MM volume may be performed in two stages. The first stage corresponds to population-based learning using population training data 130. The second stage corresponds to patient specific registration for accurate 2D-3D alignment using patient training data. Image fusion management circuitry 120 may be configured to initialize the DNNs of image fusion circuitry 122 based, at least in part, on the population-based learning.

For example, image fusion management circuitry 120 may be configured to train the DNNs of image fusion circuitry 122 using patient training data. In other words, image fusion management circuitry 120 may be configured to train image fusion circuitry 122 for patient-specific image registration through self-correction learning. The training may include a self-correcting technique for optimizing the DNN(s) to accommodate a lack of constant supervision for image registration characteristic of some interventions. Image fusion circuitry 122 may thus be configured with two registration paths. The first registration path may include DNN1 140-1 (corresponding to 2D US→3D MRI) and the second registration path may include DNN2 140-2 and DNN3 140-3 (corresponding to 2D US→3D US→3D MRI). The two paths may be configured to supervise one another during the training process. Thus, the direct image fusion training and operations, and indirect image fusion training and operations may be complementary.

Training may be performed incrementally as new images become available. During complementary training, each new batch fixes one path (i.e., direct or indirect) of the registration network(s) first and its results will be used as ground truth to train the network(s) on the other path. By training in this alternating manner, both paths may be improved and arrive at an equilibrium. A separate network may be trained for each subject and the training process may be performed off-line. In one nonlimiting example, and based on available computational resources, in training registration related GANs, the individualized training can be completed within eight hours and training the entire network on the reference data set may consume about two weeks.

In one nonlimiting example, the alternating path training may include an expectation-maximization technique. The expectation and maximization steps may be performed alternately by fixing one at a time for each iteration and estimating the parameters of the statistical models. In another nonlimiting example, for a GAN framework, the generator and discriminator may be trained alternately, i.e., each iteration step fixes the generator and updates to discriminator and vice versa. For the task of patient specific learning described herein, in some embodiments a goal is to find an equilibrium for the game of two registration players. Let $R_D$ denote the direct registration of 2D US→3D MRI and $R_I$ denote the indirect registration path. In an embodiment, the self-correction training may be realized by iteratively minimizing equations (2) and (3), where $L(\cdot)$ is the loss function measuring the difference between the registration results.

$$\theta^{(D)} = \underset{\theta^{(D)}}{\mathrm{argmin}}\, L\!\left(R_D\!\left(\theta^{(D)}\right),\, R_I^*\!\left(\theta^{(I)}\right)\right) \qquad (2)$$

-continued $$\theta^{(I)} = \underset{\theta^{(I)}}{\operatorname{argmin}} L(R_D^*(\theta^{(D)}), R_I(\theta^{(I)})) \quad (3)$$

In some embodiments, for each pair of MR and US volumes, a plurality of intensity histograms may be determined for both modalities. Eight summary statistics (mean, median, standard deviation, skewness, kurtosis, k statistic, trimmed mean and standard error of the mean) of the histograms may be determined. Then t-SNE may be used to map and plot the 16D statistics vector into 2D space.

Once patient specific registration networks are obtained as described herein, registration of a new data set can be performed by finding the k nearest neighbors of the new set and using the individualized pre-trained networks for registration. Additionally or alternatively to the histogram-based similarity as described herein, in some embodiments, local feature representation methods like SIFT (scale-invariant feature transform), MIND, and deep CNN based features may be employed. The local feature representation methods may relatively efficiently describe local spatial relationships between pixels to measure structure similarity. The final registration may be obtained as the weighted combination of multiple network outputs, where the weights are determined by the distance between the test image pair and each of the training neighbors.

Figure 1C:
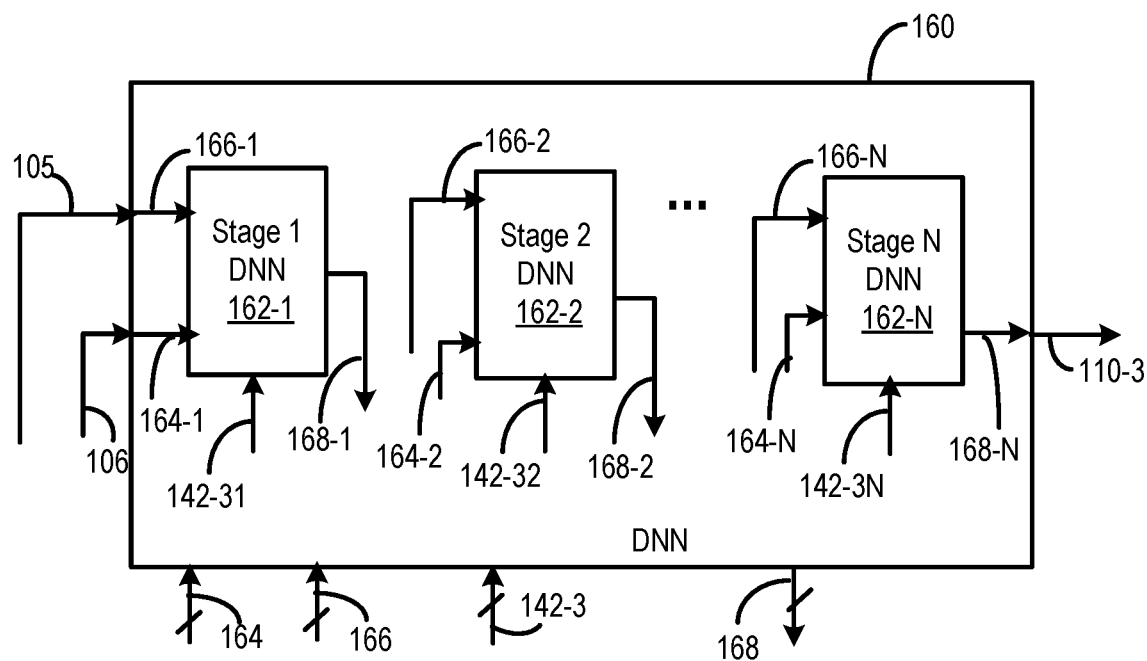

The following description may be best understood when considering FIG. 1A and FIG. 1C together. FIG. 1C is a functional block diagram for another example DNN 160 corresponding to DNN3 140-3 of FIG. 1A. In this example, DNN 160 (and thus DNN3 140-3), includes a plurality of DNN stages 162-1, 162-2, . . . , 162-N. In one nonlimiting example, N may be equal to three. However, this disclosure is not limited in this regard. It may be appreciated that DNN 160 corresponds to a coarse-to-fine multi-stage registration (MSReg) framework that may include N consecutive networks.

DNN 160 is configured to receive reconstructed 3D US volume data 105 and 3D MR volume input data 106 and to provide as output pose vector 110-3, as described herein. Image fusion management circuitry 120 is configured to manage the training and operation of DNN 160. Thus, DNN 160 is configured to receive 3D MR volume data, collectively 3D MR volume data 164 that may include initial 3D MR volume data 164-1, intermediate (i.e., updated) 3D MR volume data, e.g., 3D MR volume data 164-2, and final 3D MR volume data 164-N. DNN 160 is further configured to receive 3D US volume data, collectively 3D US volume data 166 that may include initial 3D US volume data 166-1, intermediate (i.e., updated) 3D US volume data, e.g., 3D US volume data 166-2, and final 3D US volume data 166-N. DNN 160 is configured to provide transformation vector data, collectively transformation vector data 168 to image fusion management circuitry 120. Transformation vector data 168 may include initial transformation vector data 168-1, intermediate (i.e., updated) transformation vector data, e.g., transformation vector data 168-2, and final transformation vector data 168-N. The final transformation vector data 168-N may then be utilized by image fusion management circuitry 120 to register the 3D US volume data with the corresponding 3D MR volume data.

Figure 2A:
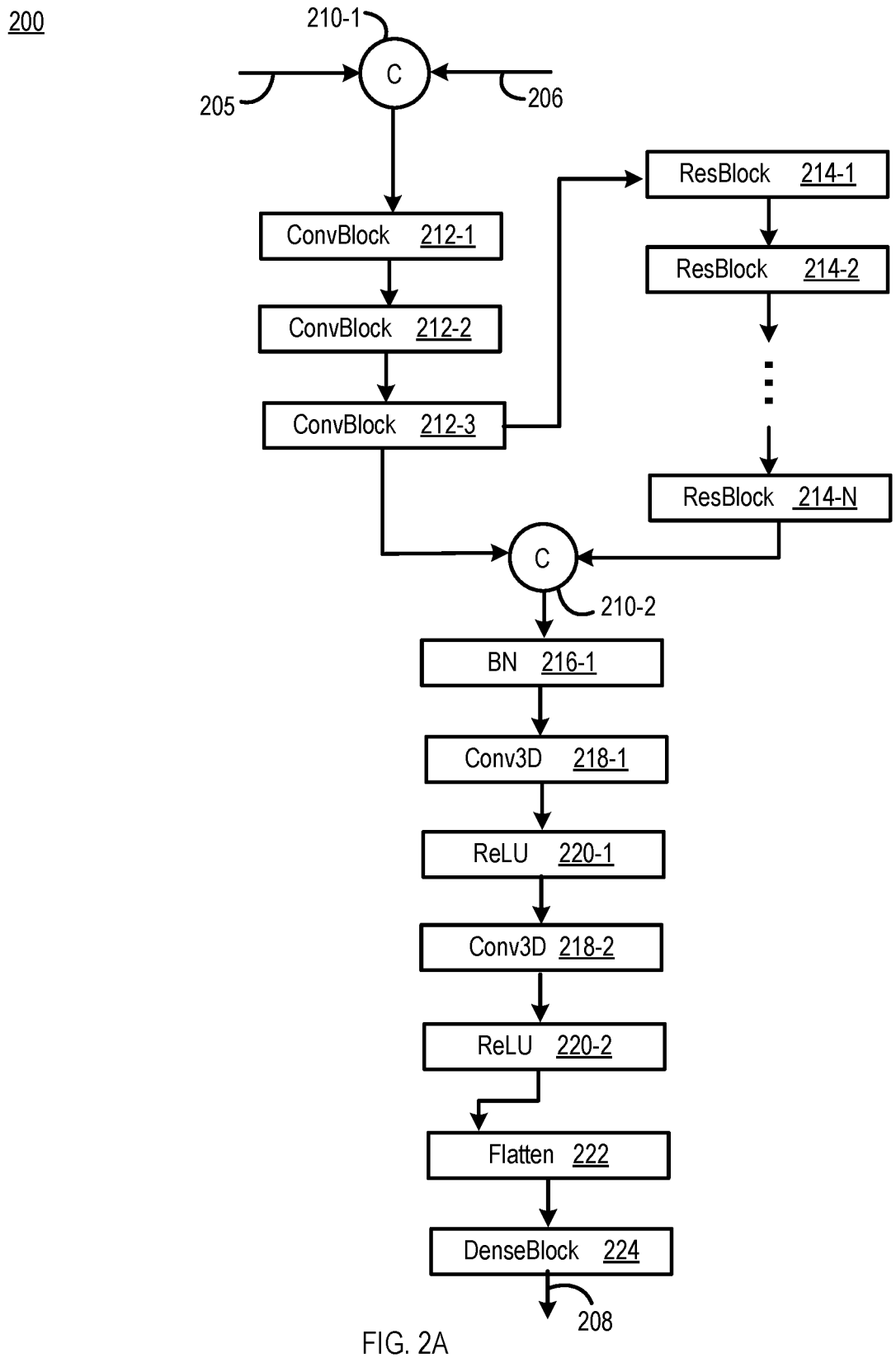
FIGS. 2A through 2C illustrate functional block diagrams of one example deep neural network (DNN) consistent with several embodiments of the present disclosure.
Figure 2B:
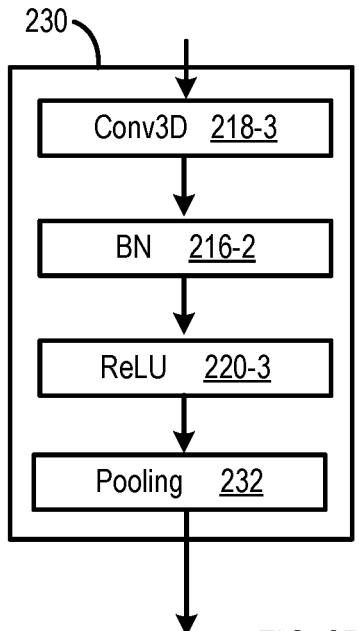
Figure 2C:
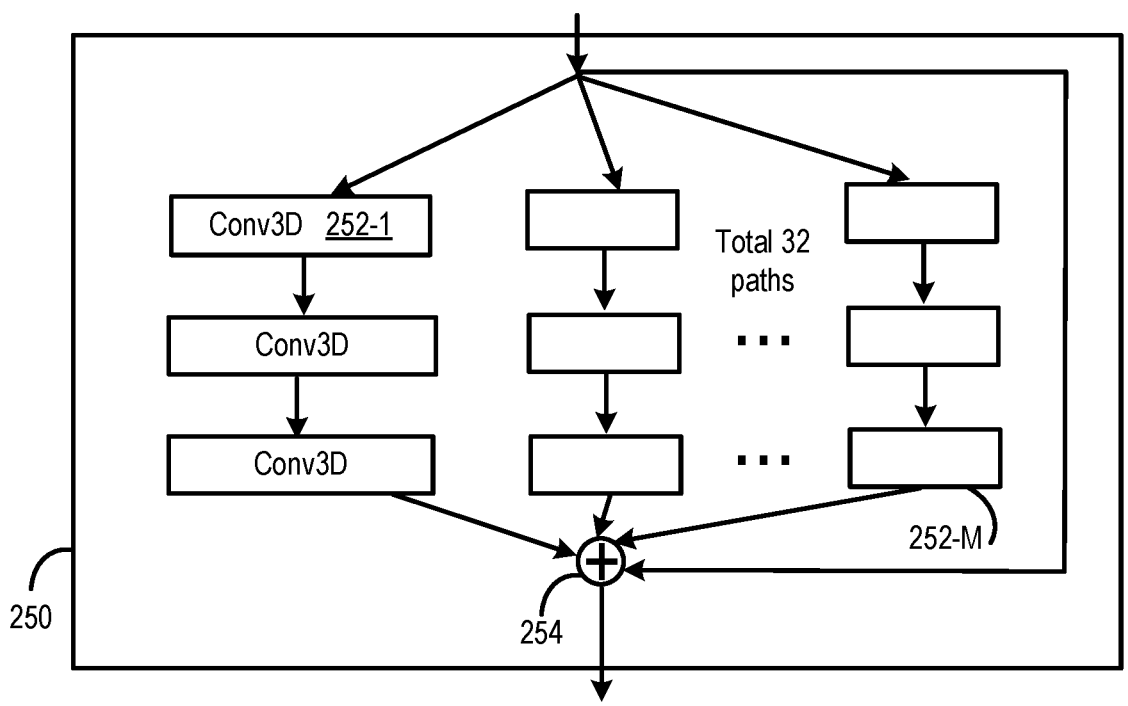

FIGS. 2A through 2C illustrate functional block diagrams of one example DNN consistent with several embodiments of the present disclosure. FIG. 2A illustrates a functional block diagram of one example DNN 200, consistent with several embodiments of the present disclosure. DNN 200 is one example of DNN 160 of FIG. 1C, is configured to receive 3D MR volume data 106 and 3D US volume data 105. FIG. 2B illustrates one example of a convolution block (ConvBlock) 230, consistent with several embodiments of the present disclosure. FIG. 2C illustrates one example of a residual block (ResBlock) 250, consistent with several embodiments of the present disclosure. Herein, "block" and "layer" the context of a neural network are used interchangeably.

Turning first to FIG. 2A, example DNN 200 is configured to receive US volume data 205 and MR volume data 206 and to provide as output a transformation vector 208, as described herein. Example DNN 200 includes a concatenate layer 210-1 configured to receive 3D US volume data 205 and MR volume data 206. Example DNN 210 further includes a sequence of three convolution blocks (ConvBlock) 212-1, 212-2, 212-3, with a first convolution block 212-1 coupled to the concatenate layer 210-1. A third convolutional block 212-3 is coupled to a second concatenate layer 210-2 and a sequence of N residual blocks (ResBlock) 214-1, 214-2, . . . , 214-N. An Nth ResBlock 214-N is coupled to the second concatenate layer 210-2. Example DNN 200 further includes a batch normalization layer (BN) 216-1, a first three-dimensional convolution layer (Conv3D) 218-1, a first rectified linear unit (ReLU) 220-1, a second Conv3D layer 218-2, a second ReLU 220-2, a flattened layer 222, and a dense block (DenseBlock) 224.

Turning now to FIG. 2B, example convolution block 230 is one example of a convolution block, e.g., convolution blocks 212-1, 212-2, and 212-3, of FIG. 2A. Example ConvBlock 230 includes a 3D convolution layer (Conv3D) 218-3, a batch normalization layer 216-2, an ReLU 220-3, and a pooling layer 232.

Turning now to FIG. 2C, example residual block 250 is one example of a residual block, e.g., residual blocks 214-1, 214-2, . . . , 214-N, of FIG. 2A. Example ResBlock 250 includes a plurality of 3D convolution layers (Conv3D) 252-1, . . . , 252-M, and a summing junction 254. The plurality of 3D convolution layers are arranged in a number of parallel paths, with each path including three 3D convolution layers in series. An input to each path is the input to the ResBlock, and an output of each path is input to the summing junction 254. An output of the ResBlock 250 corresponds to an output of the summing junction 254.

The following description of operation may be best understood when considering FIGS. 1A, 1C, and 2A through 2C together. DNN 200 corresponds to DNN 160 of FIG. 1C and thus DNN3 140-3 of FIG. 1A, in this example. Image fusion management circuitry 120 is configured to manage training and operation of image fusion circuitry 122 and DNN 160, in this example.

It may be appreciated that an error scaling technique configured to sample training data may have any target distribution based on the registration error. This data generation technique is configured to create different training data distributions, configured to enhance performance of DNN 160 and sub-networks 162-1, 162-2, . . . , 162-N, with same or different error levels.

DNN 160, configured as a coarse-to-fine multi-stage registration framework may include a network, e.g., Stage 1 DNN 162-1, relatively more adaptive to its source distribution. Since each sub-network 162-1, 162-2, . . . , 162-N may be trained using data following distributions from a given stage, there may be improvements in the registration accuracy after each iteration. It may be further appreciated that multistage DNN 160 is relatively flexible and may thus be extended to other image registration tasks.

In one nonlimiting example, transformation vectors 168-1, 168-2, ..., 168-N correspond to rigid transformation configured to estimate 6 degrees of freedom θ={$\Delta t_x$, $\Delta t_y$, $\Delta t_z$, $\Delta \alpha_x$, $\Delta \alpha_y$, $\Delta \alpha_z$}. $\Delta t$ and $\Delta \alpha$ refer to translation (e.g., in millimeters) and rotation in degrees along three directions, respectively, relative to a center of a moving image. Each DNN is configured to estimate an amount of adjusting of the moving image (e.g., US image) to improve its alignment with a fixed image (e.g., MR image). It may be appreciated that rigid registration is relatively widely used in the medical image registration field and can achieve clinically significant results.

Turning now to FIGS. 2A through 2C, the topology of DNN 200, including a plurality of pathways, is configured to enable extraction of selected features, which may facilitate training a relatively larger numbers of network layers (and thus yielding deeper networks). In one nonlimiting example, a pre-operative MR image may correspond to the fixed image and the US image may correspond to the moving image. In another example, a pre-operative MR image may correspond to the moving image and a US image may correspond to the fixed image. Thus, the fixed-moving relationship can be reversed during real-time MR-US registration.

In one nonlimiting example, to train DNN 200, a 4×4 rigid transformation matrix (composed of a 3×3 rotation matrix and 3 translation parameters) may be used as an initial transformation to roughly overlap a pair of MR and US volumes as an initialization. During the image preprocessing, each MR and US image pair may be resampled to a same resolution according to the spacing information. After applying an initial transformation, the fixed image and moving image overlap with each other. A bounding box (i.e., region of interest (ROI) of the prostate in MM may then be determined based, at least in part, on a previously performed prostate segmentation. The same ROI bound may then be used to crop the US image. The cropped ROIs may then both be resampled to a size of 32×96×96 voxels. However, this disclosure is not limited in this regard. The intensities of the two ROI volumes may then be scaled between [0, 1] and their concatenation may serve as the input to our multi-stage registration network.

DNN 200 may be constructed from 3D convolutional layers configured to extract hybrid structural features between MR and US image pairs. Residual blocks, with cardinality equaling to 16, compose the main part of the network. For DNN 200 training, shortcut connections may be used configured to avoid gradient vanishing. The extracted features (from the convolutional layers) may be applied to the dense layers to regress the parameters $\Delta t_x$, $\Delta t_y$, $\Delta t_z$, $\Delta \alpha_x$, $\Delta \alpha_y$ and $\Delta \alpha_z$. After the training, DNN 200 is configured to estimate the 6 degrees of freedom to adjust the position of the moving US images.

During the training process, the initial transformation matrices, which are used to initialize the entire workflow, may be generated by adding 6 random perturbations to ground-truth transformation matrices. These randomly generated perturbations may be stored as labels to determine a mean squared error (MSE) loss LMSE in order to update the DNN 200 parameters as:

$$L_{MSE} = \frac{1}{6}\sum_{d=1}^{6}(\theta_d^{gt} - \theta_d)^2 \qquad (4)$$

where $\theta_d^{gt}$ and $\theta_d$ are the dth degrees of freedom of the ground-truth label and network-predicted result, respectively.

SRE (surface registration error) may be used as a criterion for evaluating the registration accuracy between the US and MR image data. For network training, the optimal network parameters may be saved, based on the mean SRE of a validation set, at the end of each training epoch. To calculate SRE, a number M points located on a surface of a prostate segmentation may be used. By transforming the M surface points with the ground truth and estimated transformation matrices, a mean Euclidean distance between each corresponding point may be determined as:

$$SRE(T) = \frac{1}{M}\sum_{i=1}^{M} \|T_{gt}(P_i) - T(P_i)\|_2 \qquad (5)$$

where $T_{gt}(P_i)$ and $T(P_i)$ are the 3D coordinates of the ith surface point $P_i$ transformed by the ground-truth matrix $T_{gt}$ and testing matrix T, respectively. In this example, the moving and fixed images are sampled at 1 mm (millimeter) spacing, so SRE is measured in millimeters. However, this disclosure is not limited in this regard. Since SRE can be assumed to be linearly influenced by the translation parameters as well as by the random rotation perturbations, which vary within a relatively small range, the SRE may be scaled to a target value by scaling the 6 degrees of freedom with a same ratio.

For one-step registrations, the SRE may be determined before and after the registration to evaluate the model performance for each case. It may be appreciated that registration results with lower SRE values indicate that the final transformation matrix is closer to the ground-truth transformation matrix.

Although a fixed initialization matrix for each case may yield rapid convergence during network training, it can also result in over-fitting. To address this, a random transformation matrix may be generated for each case in the training set at each epoch. In other words, small random perturbations are introduced for the 6 degrees of freedom θ, under selected constraints. These perturbations can be added to the ground-truth transformation matrix $T_{gt}$ by −θ to generate a random initialization matrix $T_0$. Thus, the corresponding label of $T_0$ is the generated random perturbations θ, meaning that: given an initial transformation matrix $T_0$, by taking additional adjustments by the amount of θ to the moving image along 6 degrees of freedom, the moving image can be well aligned to the fixed image.

Table 1 includes Algorithm 1: Training data generation by error scaling, that may be used to generate a training set whose SRE values are drawn from the target distribution. Considering the 1-stage registration network training as an example: (1) First, random perturbations θ' may be sampled in a small range [−5, 5] at each degree of freedom; (2) the perturbations −θ' are added to the ground truth matrix Tgt to get a random matrix T' and calculate its SRE; (3) a random value may then be drawn from a target distribution (e.g. uniform distribution) and assigned as the target SRE; (4) a scaling ratio r between the target SRE and T''s SRE may then be calculated; (5) the random perturbation θ' may then be scaled to θ using the ratio r and then the perturbations −θ may be added to $T_{gt}$ to generate the initial matrix $T_0$ for training the network. Since the ratio r, which is calculated between target SRE and T'' SRE, to scale the 6 degrees of freedom θ', is used, the generated $T_0$'s SRE may be approximately equal to the target SRE. By doing this, large amounts of training data may be generated that produce SRE values drawn from any target distribution. Such a generated dataset, with theoretically infinite numbers of training samples, may improve the network's robustness and reduce the registration error.

TABLE 1

Algorithm 1: Training data generation by error scaling.
Input: Ground-truth transformation matrix Tgt of a training case
Output: Initial transformation matrix T0 and label θ used for training
1: procedure Generate_training_data($T_{gt}$)
2: {$\Delta t_x, \Delta t_y, \Delta t_z, \Delta \alpha_x, \Delta \alpha_y, \Delta \alpha_z$} ← Random_Value( )
3:                                                        ▷ Sample random perturbations
4: θ' ← {$\Delta t_x, \Delta t_y, \Delta t_z, \Delta \alpha_x, \Delta \alpha_y, \Delta \alpha_z$}
5: T' ← Update_Mat($T_{gt}$,-θ')                         ▷ Add -θ' to $T_{gt}$
6: Current_SRE ← SRE(T ')                                ▷ Compute current SRE
7: Target_SRE ← X~U(a, b)
8:           ▷ Randomly sample a value from a target distribution U(a, b)
9: r ← Target_SRE/Current_SRE                            ▷ Compute the scaling ratio r
10: θ ← θ' × r                                           ▷ Scale Current_SRE by scaling θ'
11: $T_0$ ← Update_Mat($T_{gt}$, -θ)
12: return $T_0$, θ                                      ▷ Initialization $T_0$ and its label θ

Turning again to FIG. 1C, it may be appreciated that, deep learning-based image registrations are configured to map an initial distribution to a target distribution. Since these two distributions are different, applying the same pre-trained network to iteratively compute the registration may be less than optimum. DNN 160, configured to support a coarse-to-fine multi-stage registration (MSReg), may improve the accuracy of MR-US image fusion. Such a network may be trainable in more than one way. For example, the network at each stage 162-1, 162-2, . . . , 162-N can be trained separately on a target distribution and then stacked together during the testing phase. In another example, the entire framework, i.e., DNN 160, can be trained in an end-to-end fashion.

In one nonlimiting example, the number of stages N may be 3. However, this disclosure is not limited in this regard. When training the DNN of the ith stage, the mean SRE value $\mu_i$ of its input data is calculated. A training set is then generated whose SRE may be drawn from a uniform distribution on [0, $2_{\mu_i}$ mm] for training the stage-specified network. For example, Stage 1 DNN 162-1 may be trained on the uniform-distribution $U_1$ for [0, 20 mm]; Stage 2 DNN 162-2 may be trained on the uniform distribution $U_2$ [0, 8 mm]; and Stage 3 DNN 162-N (with N=3) may be trained on the uniform distribution $U_3$ [0, 7 mm]. It may be appreciated that other types of distributions, e.g., Gaussian distribution, may be used. It may be appreciated that the Uniform distribution can produce an even diffusion of values along the search space, making the network capable of producing valid registration for extreme cases.

Thus, image fusion system 100, with DNN 160 corresponding to DNN3 140-3, as described herein, may be configured to implement network training by generating augmented datasets according to the data distributions at each stage. Training the coarse-to-fine multi-stage registration framework may include training each stage on a data distribution of its corresponding stage. It is contemplated that the coarse-to-fine network may be extended to incorporate deformable registration.

Figure 3A:
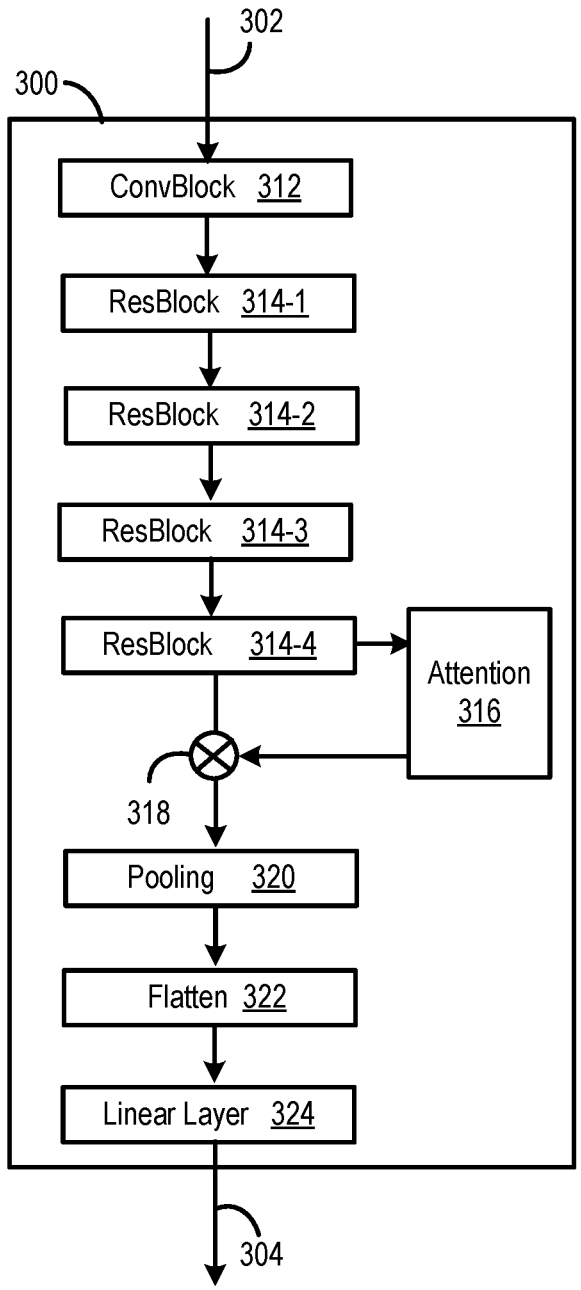
FIGS. 3A and 3B illustrate functional block diagrams of an example DNN for 3D ultrasound reconstruction consistent with an embodiment of the present disclosure.
Figure 3B:
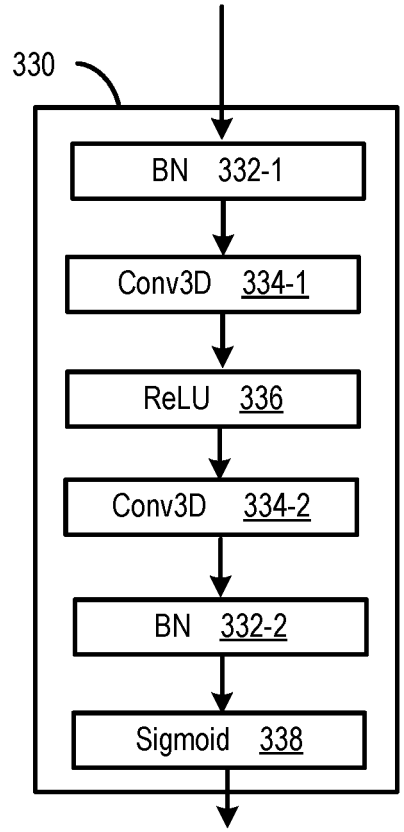

FIGS. 3A and 3B illustrate functional block diagrams of an example DNN 300 for 3D ultrasound reconstruction consistent with an embodiment of the present disclosure. FIG. 3A illustrates a functional block diagram of the example DNN 300, consistent with an embodiment of the present disclosure. FIG. 3B illustrates one example of an attention block (Attention) 330, corresponding the attention block included in example DNN 300.

Turning first to FIG. 3A, example DNN 300 is configured to receive a random video segment 302 that includes a number, N, frames and to provide as output a pose vector 304, as described herein. In this example, the pose vector 304 corresponds to a mean motion vector. Example DNN 300 includes a convolution block (ConvBlock) 312, a sequence of four residual blocks (ResBlock) 314-1, 314-2, 314-3, 314-4, a junction block 318, a pooling layer 320, a flatten block 322 and a linear layer 324. Example DNN 300 further includes an attention block 316 coupled to a fourth residual block 314-4 and to the junction block 318. ConvBlock 312 is configured to receive the random video segment (N consecutive frames) 302 and the linear layer 324 is configured to provide as output the mean motion vector 304. The ConvBock 312 corresponds to convolutional block 230 of FIG. 2B. The residual blocks 314-1, 314-2, 314-3, 314-4 correspond to residual block 250 of FIG. 2C.

Turning now to FIG. 3B, attention block 330 is one example of an attention block, e.g., attention block 316, of FIG. 3A. Example attention block 330 includes a first batch normalization layer 332-1, a first 3D convolution layer (Conv3D) 334-1, an ReLU 336, a second Conv3D layer 334-2, and a pooling layer 232, a second batch normalization layer 332-2, and a sigmoid layer 338.

In an embodiment, DNN 300 corresponds to a deep contextual learning network ("DCL-Net"), that is configured to efficiently exploit an image feature relationship between US frames and to then reconstruct 3D US volumes without a tracking device. DCL-Net 300 is configured to utilize 3D convolution over a US video segment for feature extraction. The embedded self-attention module 316 is configured to cause the network 300 to focus on the speckle-rich areas for better spatial movement prediction. DCL-Net 300 may include a case-wise correlation loss configured to stabilize the training process for improved accuracy.

The DCL-Net 300 is configured for sensorless freehand 3D ultrasound (US) reconstruction, and is thus configured to receive a plurality of consecutive 2D US frames as input, and to estimate a trajectory of a corresponding US probe by relatively efficiently exploiting contextual information included in the plurality of consecutive frames. The attention module 316 is embedded into the network architecture and is configured to cause DCL-Net 300 to focus on a speckle-rich image area to utilize any decorrelation information that may be present between frames. In some embodiments, a case-wise correlation loss may be implemented configured to enhance a discriminative feature learning and to prevent over-fitting.

Each frame in a plurality of consecutive US frames may correspond to an EM tracked vector that contains respective position and respective orientation information of each frame. The vector may be converted to a 3D homogeneous transformation matrix M=[R T; 0 1], where R is a 3×3 rotation matrix and T is a 3D translation vector.

A goal of 3D ultrasound reconstruction is to obtain a relative spatial position of two or more consecutive US frames. Without loss of generality, two neighboring frames are used as an illustrative example. In this example, $I_i$ and $I_{i+1}$ denote two consecutive US frames with corresponding transformation matrices $M_i$ and $M_{i+1}$, respectively. A relative transformation matrix $M_i'$ can be determined as $M_i'=M_{i+1}M_i^{-1}$. By decomposing $M_i'$ into 6 degrees of freedom $$\theta_i = \{t_x, t_y, t_z, \alpha_x, \alpha_y, \alpha_z\}_i \qquad (6)$$

that contains the translations, t, in millimeters and rotations, α, in degrees. $\theta_i$ determined based, at least in part, on EM tracking data may be utilized as the ground-truth for network training.

DCL-Net 300 is one example deep contextual learning network and includes a ResNext model. DCL-Net 300 3D residual blocks and other types of CNN layers, as described herein. Any skip connections may be configured to help preserve gradients to train relatively deep networks. A plurality of pathways (i.e., cardinalities) are configured to enable extraction of selected features. 3D convolutional kernels may relatively better extract the feature mappings along the axis of channel, corresponding to a temporal direction. DCL-Net 300 may thus be configured to focus on a relatively slight displacement of image features between consecutive frames. DCL-Net 300 can thus be trained to connect these speckle correlated features to estimate the relative position and orientation.

During the training process, a sequence of N frames is stacked with height and width denoted by H and W, respectively, to form a 3D input volume with shape N×H×W. $\{\theta_i | i=1, \ldots, N-1\}$ denotes a plurality of relative transform parameters between neighboring frames. Mean parameters:

$$\bar{\theta} = \frac{1}{N-1} \sum_{i=1}^{N-1} \theta_i \qquad (7)$$

may be used. Since a magnitude of motion between two frames is relatively small, the mean may effectively smooth noise associated with probe motion. In practice, the output layer may not change when a number of input frames changes. A sliding window of N frames is applied to a video sequence with a window size N. Inter-frame motion of two neighboring frames may then correspond to an average motion computed in a number of batches.

Attention block 316 is configured to focus DCL-Net 300 on a specific region of an image that may contain salient information. For example, in a 3D US volume reconstruction task, regions with strong speckle patterns for correlation are of relatively high importance in estimating the transformations. Example attention block 330 corresponds to a self-attention block and is configured to take the feature maps produced by the last residual block as input and then output an attention map. Relatively highly informative regions may thus be assigned relatively greater weights.

A loss function associated with DCL-Net 300 may include, for example, two components: mean squared error (MSE) loss and a case-wise correlation loss. Use of MSE loss alone can lead to the smoothed estimation of the motion and thus the trained network tends to memorize the general style of how the clinicians move the probe, i.e. the mean trajectory of the ultrasound probes. The case-wise correlation loss is based on a Pearson correlation coefficient and is configured to emphasize a specific motion pattern of a scan.

To determine the case-wise correlation loss, K video segments with each having N frames may be randomly sampled from a US video. Correlation coefficients between the estimated motion and the ground truth mean may be determined for each degree-of-freedom and the loss is denoted as:

$$L_{corr} = 1 - \frac{1}{6}\sum_{d=1}^{6} \frac{\text{Cov}(\bar{\theta}_d^{GT}, \bar{\theta}_d^{out})}{\sigma(\bar{\theta}_d^{GT})\sigma(\bar{\theta}_d^{out})} \qquad (8)$$

where Cov is the covariance and σ corresponds to standard deviation. The total loss is then the summation of the MSE loss and the case-wise correlation loss.

Thus, DCL-Net 300 is configured to extract information among a plurality of US frames and may improve the US probe trajectory estimation. DCL-Net 300 may be utilized, for example, by image fusion management circuitry 120 and 3D US volume reconstruction circuitry. However, this disclosure is not limited in this regard.

It may be appreciated that a reconstructed 3D US volume may provide relatively more context information compared to a sequence of 2D scanning frames. As used herein, 2D scans corresponds to 2D US frames. The context information may be helpful for various clinical applications including, but not limited to, ultrasound-guided prostate biopsy. 3D volume reconstruction from freehand 2D scans can be relatively challenging without the use of external tracking devices. Some deep learning based methods may be configured to directly estimate inter-frame motion between consecutive ultrasound frames. Such algorithms may be specific to particular transducers and scanning trajectories associated with the training data, which may not be generalized to other image acquisition settings. In an embodiment, such data acquisition difference may correspond to a domain shift and a domain adaptation strategy may be configured to adapt deep learning algorithms to data acquired with different transducers. For example, feature extractors that generate transducer-invariant features from different datasets may be trained by minimizing a difference between deep features of paired samples in a latent space. A domain adaptation technique, consistent with the present disclosure, may align different feature distributions while preserving the transducer-specific information for universal freehand ultrasound volume reconstruction.

For example, 3D volume reconstruction circuitry 121 may include a DNN, e.g., DNN 300 of FIGS. 3A and 3B. DNN 300 may be trained using, e.g., transrectal (TR) US frame data, as described herein. In operation, providing, e.g., 2D transabdominal (TA) US frame data to the trained DNN 300 may result in performance degradation for reconstructing 3D US volume. While both TR and TA scans may be used to facilitate prostate cancer diagnosis, each has distinct motion trajectories and imaging properties. As used herein, a source domain (e.g., TR US data) corresponds to a dataset which serves as training data of the DNN, and target domain (e.g., TA US data) corresponds to a new dataset where the trained DNN is to be applied. Thus, reconstructing US volume with 2D US frame data from different US transducers corresponding to a domain adaptation problem.

A goal is to make DNN 300 accurately predict the relative position between two US frames. In an embodiment, a paired-sampling strategy with a discrepancy loss may be utilized to transfer task-specific feature learning from source domain to target domain. It is contemplated that if two US video sub-sequences acquired using different transducers have similar motion trajectories, they should be close to each other in the latent feature space.

In an embodiment, domain adaptation techniques may be applied to US volume reconstruction. For example, a paired-sampling strategy with feature discrepancy minimization may be configured to facilitate model (i.e., DNN} adaptation from the source domain to the target domain. This strategy may be designed for registration-related domain adaptation problems In an embodiment, a DNN 300 may be configured to extract domain-invariant features while preserving task-specific feature learning.

For example, 3D ultrasound reconstruction operations may include obtaining a relative spatial position of two or more consecutive 2D US frames. For example, a small subsequence containing N consecutive frames may correspond to one sample unit. For example, a relative transformation matrix may be determined and may be decomposed into 6 degrees of freedom (DOF), $$Y = \{t_x, t_y, t_z, \alpha_x, \alpha_y, \alpha_z\} \tag{9}$$

which contains translations in millimeters and rotations in degrees. The DNN may then be configured to capture one video subsequence as the input for estimating the transformation parameters. Each subsequence's corresponding DOF vector may correspond to a respective ground truth label during each the training process.

It may be appreciated that 2D US transducers may have very different scanning trajectories for different applications (e.g., TR vs. TA), that may result in label bias and can substantially impair the network performance. Initially, a pre-processing operation may be performed configured to roughly align a video sequence trajectory in 3D space. For example, the US videos may be scaled to the same resolution and align the first frame of the video sequences to the same position. The sequence rotating center (transducer's head) may be configured to overlap with the origin (0; 0; 0) of the 3D coordinate system. Thus, the label distributions of source domain and target domain may be aligned together. Before the trajectory alignment, the source and target DOF label distributions may be separated into two clusters. After the alignment, the label distributions are merged together, showing a smooth aX transition pattern. The trajectory alignment is configured to ensure that the DNN's performance will not be impaired by the gap in label distributions.

For example, a source domain dataset (TR US scans) may be written as $\{X_s|Y_s\}$, where each image sample $X_s$ represents a subsequence of N=5 consecutive frames and its corresponding label $Y_s$ is a 6 DOF vector. In addition, a labeled but relatively smaller dataset on target domain (transabdominal scans) $\{X_t|Y_t\}$. In an embodiment, a method for transducer adaptive ultrasound volume reconstruction (TAUVR) may include three consecutive operations.

Initially, a convolutional feature extractor $G_s$ and a DOF regressor $R_s$ may be trained in the source domain in an end-to-end fashion. In this example, the input to $G_s$ is a N×W×H subsequence tensor and the output is a 2048 D feature vector. The DOF regressor corresponds to a linear layer that outputs 6 values for DOF regression. $G_s$ and $R_s$ may be jointly trained by minimizing the mean squared error (MSE) loss between network's output and ground truth DOF labels.

A feature extractor $G_t$ may then be trained on target domain configured to produce both domain-invariant feature while preserving task-specific information. $G_t$ may then be initialized with the parameters of $G_s$ and may share the identical structure. $G_s$'s parameters are fixed in this operation. A source domain subsequence pool may be created in which each TR video subsequence has a corresponding DOF label vector. During adaptation training, for each random target subsequence sample $x_t$, its DOF vector $y_t$ may be determined based on labeling information. The pool may be searched to find a source domain subsequence $x_s$ that has the closest motion vector as $y_t$. The subsequence may serve as the input to corresponding networks, yielding a pair of latent feature vectors denoted as:

$$v_s = G_s(x_s); v_t = G_t(x_t) \tag{10}$$

$G_t$ is trained by minimizing the discrepancy loss LD, which is the L2 norm between the two generators' output feature vectors:

$$L_D = \frac{1}{P} \sum_{p=1}^{P} \|v_s^p - v_t^p\|_2 \tag{11}$$

where P denotes the total number of sampled pairs within one training epoch. The intuition of this paired sampling strategy is to establish correspondence between source and target subsequences: when two subsequences from different domains have similar motion, their extracted feature vectors may be close to each other in the latent space. This paired sampling strategy takes rich information in the labeled source dataset as a reference to guide task-specific features learning in the target domain. Since the labels of target domain data may be used for sampling subsequence pairs while not directly contributing to the loss function, the method may be categorized as a weakly-supervised method.

An inference testing phase on target domain data does not involve any parameters update. The network used in this operation may be the concatenation of $G_t$ and $R_s$, from above. For a full-length US video sequence in the target domain test set, a sliding window procedure may be sued to get the DOF motion vector prediction for every subsequence. By placing each frame into 3D space accordingly, a 3D US image volume can be reconstructed. The testing phase does not require any tracking devices and CNN estimates US frames relative position.

Figure 4:
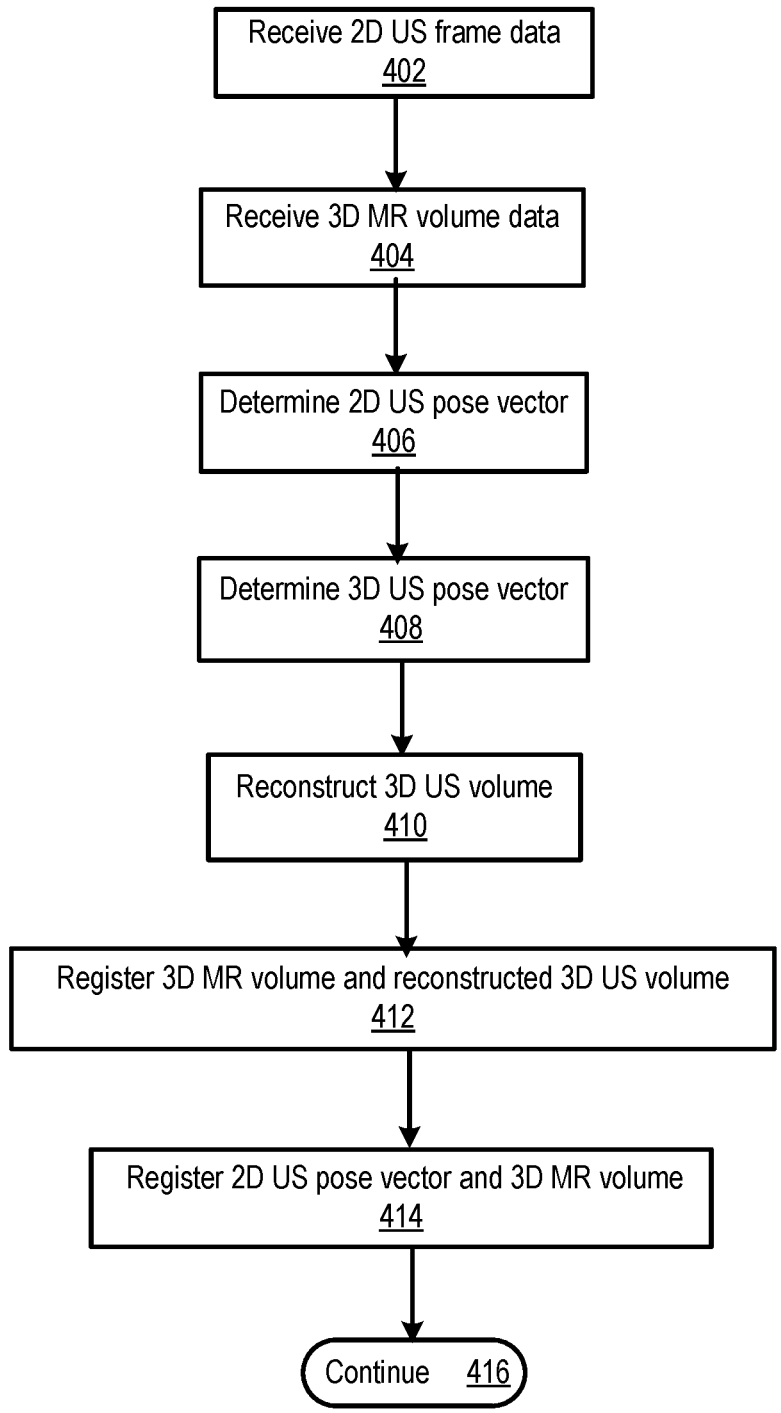
FIG. 4 a flowchart of image fusion operations according to various embodiments of the present disclosure.

FIG. 4 a flowchart of image fusion operations according to various embodiments of the present disclosure. In particular, the flowchart 400 illustrates registering 2D US frame data with 3D MR volume data. The operations may be performed, for example, by image fusion management circuitry 120, and/or image fusion circuitry 122 of FIG. 1.

Operations of this embodiment may begin with receiving 2D US frame data at operation 402. 3D MR volume data may be received at operation 404. A 2D US pose vector may be determined at operation 406. For example, the 2D US pose vector may be determined by a first DNN. A 3D US pose vector may be determined at operation 408. For example, the 3D US pose vector may be determined by a second DNN. A 3D US volume may be reconstructed at operation 410. For example, the 3D US volume may be reconstructed based, at least in part, on the 3D US pose vector. The 3D MR volume and reconstructed 3D US volume may be registered at operation 412. For example, the registering of operation 412 may be performed by a third DNN. A 2D US pose vector and the 3D MR volume may be registered at operation 414. Program flow may continue at operation 416.

Thus, 2D US frame data may be registered (i.e., fused) with 3D MR volume data.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc.

Memory 112 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively system memory may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. An apparatus for registering a two dimensional (2D) ultrasound (US) frame and a three dimensional (3D) magnetic resonance (MR) volume, the apparatus comprising:
   a first deep neural network (DNN) configured to determine a 2D US pose vector based, at least in part, on 2D US frame data and 3D MR volume data, the pose vector being configured to provide relative position and orientation of the 2D US frame with respect to the MR volume; and
   an image fusion management circuitry configured to register the 2D US frame data and the 3D MR volume data, the registering based, at least in part, on the 2D US pose vector.

2. The apparatus of claim 1, further comprising a second DNN configured to determine a 3D US pose vector based, at least in part, on the 2D US frame data;
   a 3D US volume reconstruction circuitry configured to reconstruct a 3D US volume based, at least in part, on the 3D US pose vector; and
   a third DNN configured to determine a transformation relating the 3D MR volume and the 3D US volume, wherein the registering of the 2D US frame data and the 3D MR volume data is based, at least in part, on the transformation.

3. The apparatus of claim 2, wherein the first DNN and the second and third DNNs are trained alternatingly.

4. The apparatus of claim 2, wherein the third DNN comprises a plurality of DNN stages configured for coarse-to-fine multi-stage registration.

5. The apparatus of claim 2, wherein the third DNN is configured as a generative adversarial network (GAN).

6. The apparatus of claim 1, wherein the first DNN is initially trained using population data and is subsequently trained using patient data.

7. A method for registering a two dimensional (2D) ultrasound (US) frame and a three dimensional (3D) magnetic resonance (MR) volume, the method comprising:
   determining, by a first deep neural network (DNN), a 2D US pose vector based, at least in part, on 2D US frame data and 3D MR volume data, the pose vector providing relative position and orientation of the 2D US frame with respect to the MR volume; and
   registering, by an image fusion management circuitry, the 2D US frame data and the 3D MR volume data, the registering based, at least in part, on the 2D US pose vector.

8. The method of claim 7, further comprising determining, by a second DNN, a 3D US pose vector based, at least in part, on the 2D US frame data;
   reconstructing, by a 3D US volume reconstruction circuitry, a 3D US volume based, at least in part, on the 3D US pose vector; and
   determining, by a third DNN, a transformation relating the 3D MR volume and the 3D US volume, wherein the registering of the 2D US frame data and the 3D MR volume data is based, at least in part on the transformation.

9. The method of claim 8, wherein the first DNN and the second and third DNNs are trained alternatingly.

10. The method of claim 8, wherein the third DNN comprises a plurality of DNN stages configured for coarse-to-fine multi-stage registration.

11. The method of claim 8, wherein the third DNN is configured as a generative adversarial network (GAN).

12. The method of claim 7, wherein the first DNN is initially trained using population data.

13. The method of claim 12, wherein the first DNN is trained using patient data.

14. A system for registering a two dimensional (2D) ultrasound (US) frame and a three dimensional (3D) magnetic resonance (MR) volume, the system comprising:
- a processor;
- a memory;
- input/output circuitry;
- a first deep neural network (DNN) configured to determine a 2D US pose vector based, at least in part, on 2D US frame data and 3D MR volume data, the pose vector being configured to provide relative position and orientation of the 2D US frame with respect to the MR volume; and
- an image fusion management circuitry configured to register the 2D US frame data and the 3D MR volume data, the registering based, at least in part, on the 2D US pose vector.

15. The system of claim 14, further comprising a second DNN configured to determine a 3D US pose vector based, at least in part, on the 2D US frame data;
- a 3D US volume reconstruction circuitry configured to reconstruct a 3D US volume based, at least in part, on the 3D US pose vector; and
- a third DNN configured to determine a transformation relating the 3D MR volume and the 3D US volume,
  - wherein the registering of the 2D US frame data and the 3D MR volume data is based, at least in part on the transformation.

16. The system of claim 15, wherein the first DNN and the second and third DNNs are trained alternatingly.

17. The system of claim 15, wherein the third DNN comprises a plurality of DNN stages configured for coarse-to-fine multi-stage registration.

18. The system of claim 15, wherein the third DNN is configured as a generative adversarial network (GAN).

19. The system of claim 14, wherein the first DNN is initially trained using population data and is subsequently trained using patient data.

20. A computer readable storage device having stored thereon instructions that when executed by one or more processors result in the following operations comprising:
- the method according to any one of claims 7 through 13.

* * * * *